(12) United States Patent
Shehada

(10) Patent No.: US 7,264,592 B2
(45) Date of Patent: Sep. 4, 2007

(54) SCANNING DEVICES FOR THREE-DIMENSIONAL ULTRASOUND MAMMOGRAPHY

(75) Inventor: Ramez E. N. Shehada, La Mirada, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 67 days.

(21) Appl. No.: 10/607,878

(22) Filed: Jun. 27, 2003

(65) Prior Publication Data

US 2004/0064046 A1 Apr. 1, 2004

Related U.S. Application Data

(60) Provisional application No. 60/392,343, filed on Jun. 28, 2002.

(51) Int. Cl.
*A61B 8/00* (2006.01)

(52) U.S. Cl. ...... 600/444; 128/915

(58) Field of Classification Search ........ 600/407–472; 73/625, 626; 367/7, 11, 107, 130, 138; 128/915, 128/916
See application file for complete search history.

(56) References Cited

U.S. PATENT DOCUMENTS

| | | | |
|---|---|---|---|
| 3,940,625 A | 2/1976 | Hounsfield | |
| 3,963,933 A * | 6/1976 | Henkes, Jr. | 378/20 |
| 4,075,883 A * | 2/1978 | Glover | 73/607 |
| 4,105,018 A | 8/1978 | Greenleaf et al. | |
| 4,222,274 A * | 9/1980 | Johnson | 73/607 |
| 4,233,988 A * | 11/1980 | Dick et al. | 600/445 |
| 4,252,125 A * | 2/1981 | Iinuma | 600/444 |
| 4,282,880 A * | 8/1981 | Gardineer et al. | 600/437 |
| 4,341,222 A * | 7/1982 | Gardineer et al. | 600/437 |
| 4,478,083 A * | 10/1984 | Hassler et al. | 73/620 |
| 4,485,819 A | 12/1984 | Igl | |
| 4,509,368 A | 4/1985 | Whiting et al. | |
| 5,479,927 A * | 1/1996 | Shmulewitz | 600/445 |
| 6,122,542 A | 9/2000 | Lee et al. | |
| 6,216,025 B1 * | 4/2001 | Kruger | 600/407 |
| 6,304,770 B1 | 10/2001 | Lee et al. | |
| 6,409,668 B1 | 6/2002 | Wollschlaeger | |
| 6,423,081 B1 | 7/2002 | Lee et al. | |
| 6,475,150 B2 | 11/2002 | Haddad | |
| 6,480,565 B1 | 11/2002 | Ning | |
| 7,094,205 B2 * | 8/2006 | Marmarelis | 600/448 |

* cited by examiner

*Primary Examiner*—Francis J. Jaworski
(74) *Attorney, Agent, or Firm*—McDermott Will & Emery LLP

(57) ABSTRACT

A breast tomography scanner including a stationary chamber configured to hold fluid, a movable chamber within the stationary chamber configured to hold fluid, and breast scanning apparatus. Various configurations for housing the ultrasonic transducers are disclosed, along with filling and draining apparatus, leakage protections turbulence-reduction configurations and control systems.

28 Claims, 6 Drawing Sheets

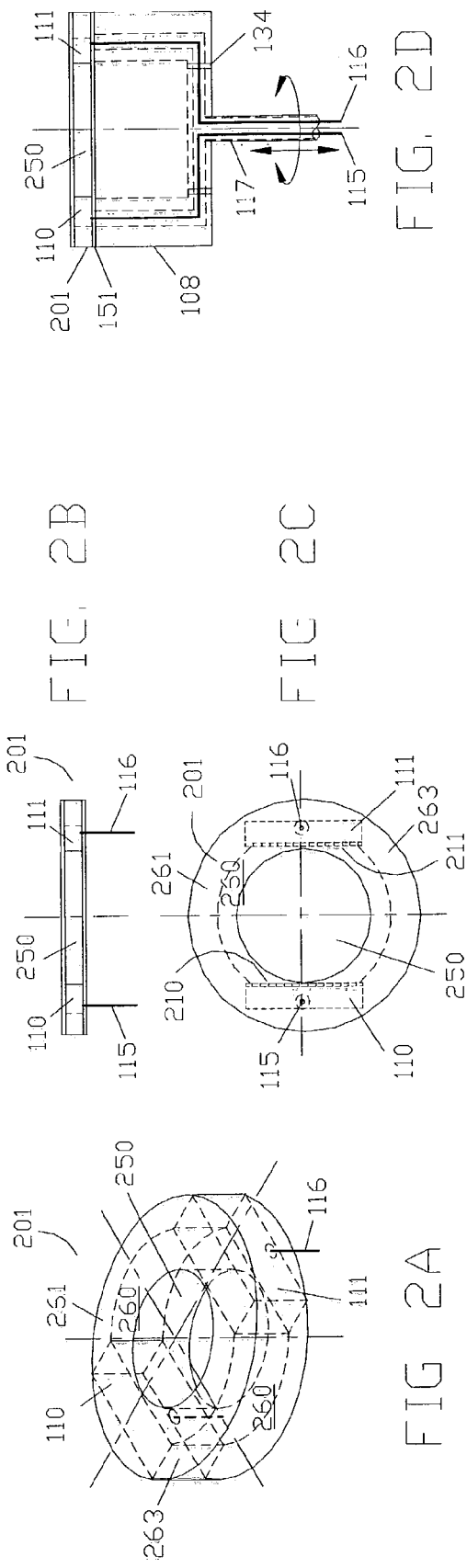
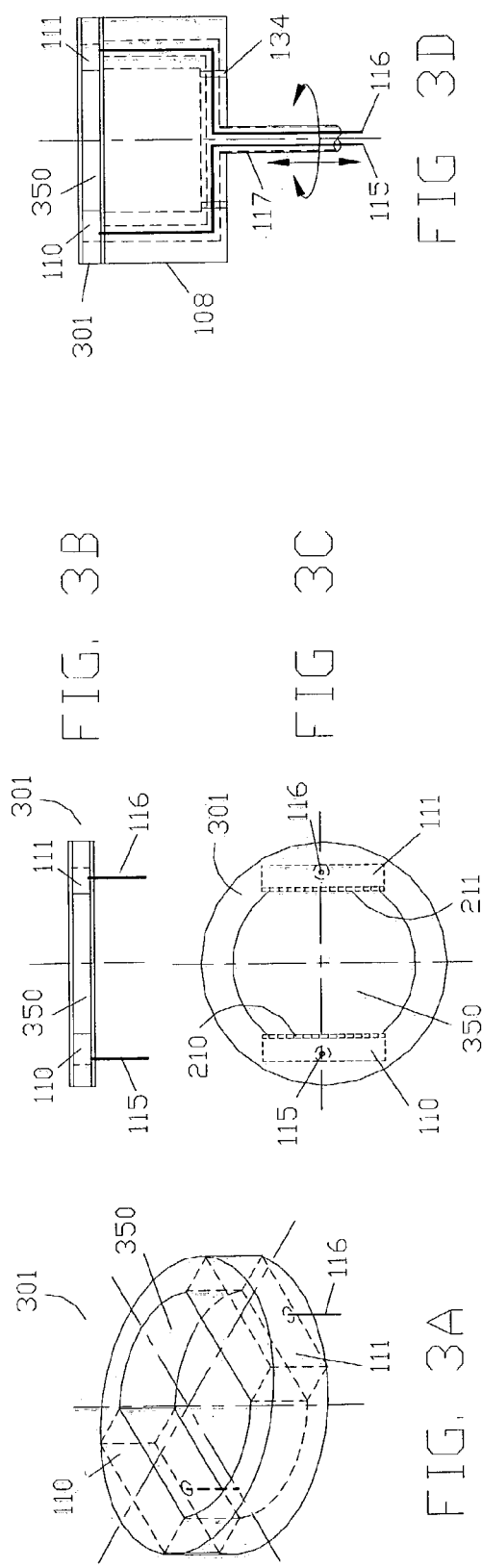

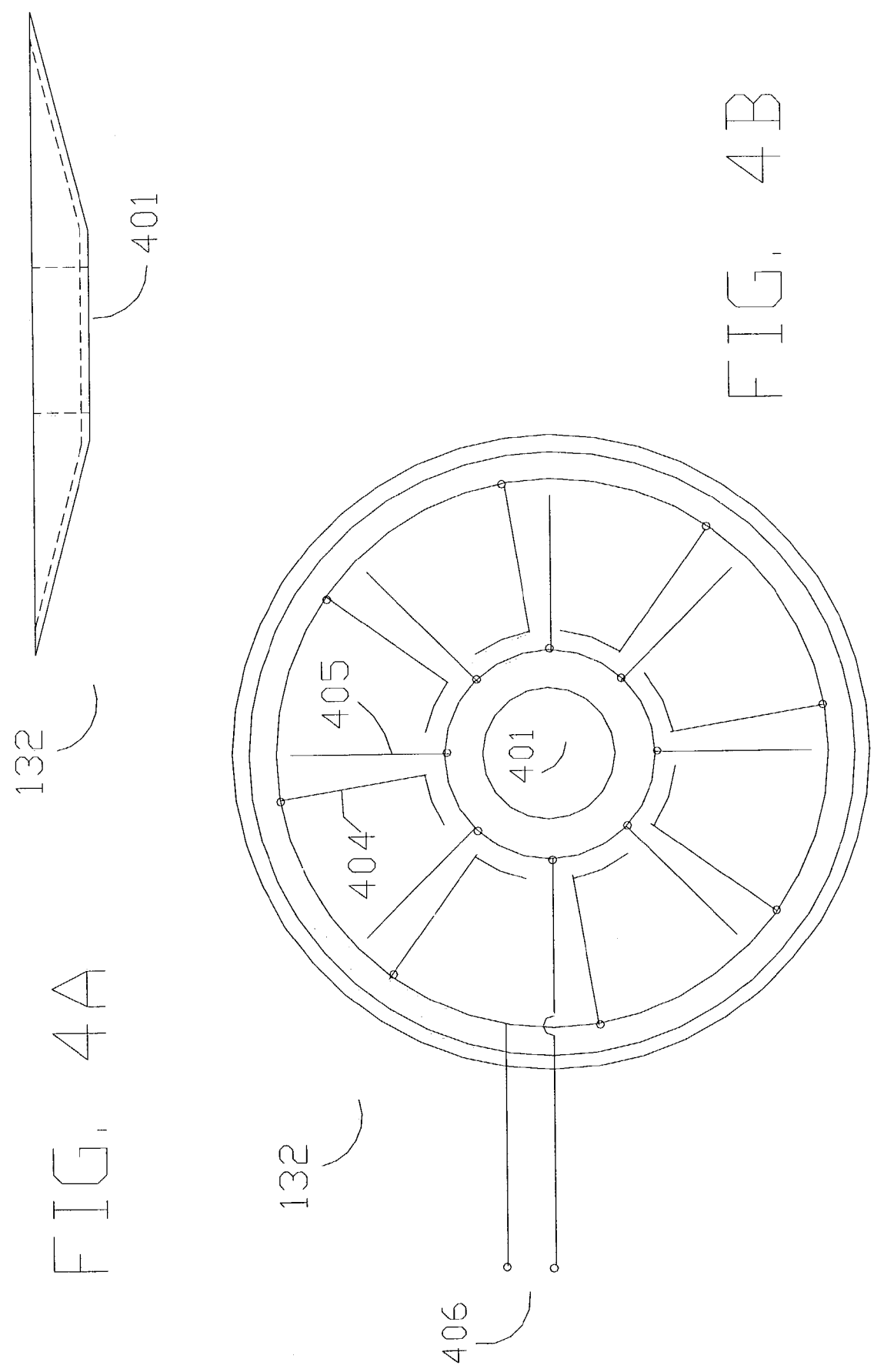

SCANNING DEVICES FOR THREE-DIMENSIONAL ULTRASOUND MAMMOGRAPHY

CROSS-REFERENCE TO RELATED APPLICATION

This application is related to and claims the benefit of U.S. Provisional Application Ser. No. 60/392,343, filed Jun. 28, 2002 entitled "Scanning Devices for Three-Dimensional Ultrasound Mammography," the content of which is incorporated herein by reference as though fully set forth.

BACKGROUND OF INVENTION

1. Field of Invention

This invention relates to tomography and, more particularly, to three-dimensional, ultrasound tomographic mammography.

2. Description of Related Art

One approach to ultrasound breast tomography has been to have the female subject lie in the prone position in a special bed and suspend one of her breasts into a container filled with acoustical coupling fluid. Ultrasonic transducers are arranged to rotate about the suspended breast in the fluid-filled container. Transmission or reflection projections are measured and used to reconstruct tomographic images.

The rotation of the ultrasonic transducers around the breast can cause currents in the fluid and, in turn, movement of the breast during the scanning process. This can distort the tomographic images.

One effort at dealing with this problem is set forth in a U.S. Pat. No. 4,105,018, issued on Aug. 8, 1978. FIG. 3 of this patent illustrates a stationary pedestal on which the lowest portion of the breast is rested. Unfortunately, the use of such a pedestal can complicate the mechanics and process by requiring a height adjustment mechanism and associated process to accommodate breasts of different sizes. Also, it may not prevent the turbulence in the fluid from causing upper portions of the breast to vibrate during the scanning process.

Another approach is to surround the breast with a stationary foil, as shown in FIG. 7 of U.S. Pat. No. 4,485,819, issued on Dec. 4, 1984. Unfortunately, this approach may interfere with the ultrasound signals and can restrict the ability of the system to scan portions of the breast close to the chest.

SUMMARY OF THE INVENTION

A breast tomography scanner may include a stationary chamber configured to hold fluid; a movable chamber within the stationary chamber configured to hold fluid, to move relative to the stationary chamber, and to receive a breast; and breast scanning apparatus configured to scan the breast received by the movable chamber.

The breast scanning apparatus may include an ultrasonic transmitter and an ultrasonic receiver coupled to the movable chamber and positioned to receive the breast between them.

The movable chamber may have an upper rim and the ultrasonic transmitter and the ultrasonic receiver may be located at the upper rim.

The breast tomography scanner may also include a housing affixed to the upper rim in which the ultrasonic transmitter and ultrasonic receiver are contained. The housing may include a recessed cavity surrounding the ultrasonic transmitter and the ultrasonic receiver.

The movable chamber may be configured to rotate about a vertical axis within the stationary chamber.

The movable chamber may be configured to move vertically.

The movable chamber may have one or more fluid communication channels other than at its top configured to allow fluid to flow between the movable chamber and the stationary chamber.

The movable chamber may have a bottom 113 and the fluid communication channel(s) may be in the bottom 113. The movable chamber may have a cylindrical wall and the fluid communication channel(s) may be adjacent the wall.

The movable chamber may have a cylindrical wall and the fluid communication channel(s) may be in the cylindrical wall. The movable chamber may have a bottom and the fluid communication channel(s) may be adjacent the bottom.

The breast tomography scanner may include a shaft extending though the stationary chamber and affixed to the movable chamber.

The breast tomography scanner may include a leak-resistant bearing between the shaft and the stationary chamber.

The breast tomography scanner may include a collection chamber positioned beneath the leak-resistant bearing and configured to collect fluid that leaks past the leak-resistant bearing. A suction device may be connected to the collection chamber to remove fluid collected in the collection chamber.

The breast tomography scanner may include a leak collection tray positioned beneath the collection chamber to collect fluid that leaks past the collection chamber. An alarm may be in communication with the collection tray and configured to sound in the event that fluid leaks onto the leak collection tray. A power shut off circuit may be in communication with the collection tray and configured to remove power from the breast tomography scanner in the event that fluid leaks onto the leak collection tray.

The shaft may have an interior, the breast scanning apparatus may include an ultrasonic transducer coupled to the movable chamber, and electrical wires may be attached to the ultrasonic transducer that pass though the interior of the shaft. The electrical wires may be protected from exposure to fluid that is placed in the movable chamber. The electrical wires may be attached to a slip ring assembly mounted to the shaft.

The movable chamber may be configured to hold a fluid up to a first level and the stationary chamber may be configured to hold fluid up to a level that is higher than the first level.

The breast tomography scanner may include a chamber filling pump configured to cause fluid to fill the movable chamber and the stationary chamber and a processor configured to control the operation of the chamber filling pump such that the chamber filling pump causes the fluid level in both the movable chamber and the stationary chamber to exceed the first level.

The stationary chamber and the movable chamber may be configured such that the level of fluid within both of them equalizes.

The breast tomography scanner may include a table top having a top surface and a bottom surface positioned above the movable chamber and an opening in the table top extending from the top surface to the bottom surface, positioned above the movable chamber, and configured to receive a breast.

The breast tomography scanner may include a drain positioned under the top surface of the table and configured to prevent fluid from flowing from the stationary chamber or movable chamber to the top surface of the table. The drain may be positioned between the top and bottom surface of the table top and be in fluid communication with the opening.

The top surface, but not the bottom surface, may be tapered downwardly in the area of the opening.

The breast tomography scanner may include a drain at the bottom of the stationary chamber to drain fluid from the chamber and a slanted surface at the bottom of the stationary chamber configured to direct fluid towards the drain.

These as well as still further features, benefits and objects will now become clear upon an examination of the following detailed description of illustrative embodiments and the attached drawings.

BRIEF DESCRIPTION OF DRAWINGS

FIGS. 2A-D illustrate a housing for transducers that may be used in a breast tomography scanner.

FIGS. 3A-D illustrate another embodiment of a housing for transducers that may be used in a breast tomography scanner.

FIGS. 4A-B illustrate a leak collection and detection tray that may be used in a breast tomography scanner.

DETAILED DESCRIPTION OF ILLUSTRATIVE EMBODIMENTS

Figure 1:
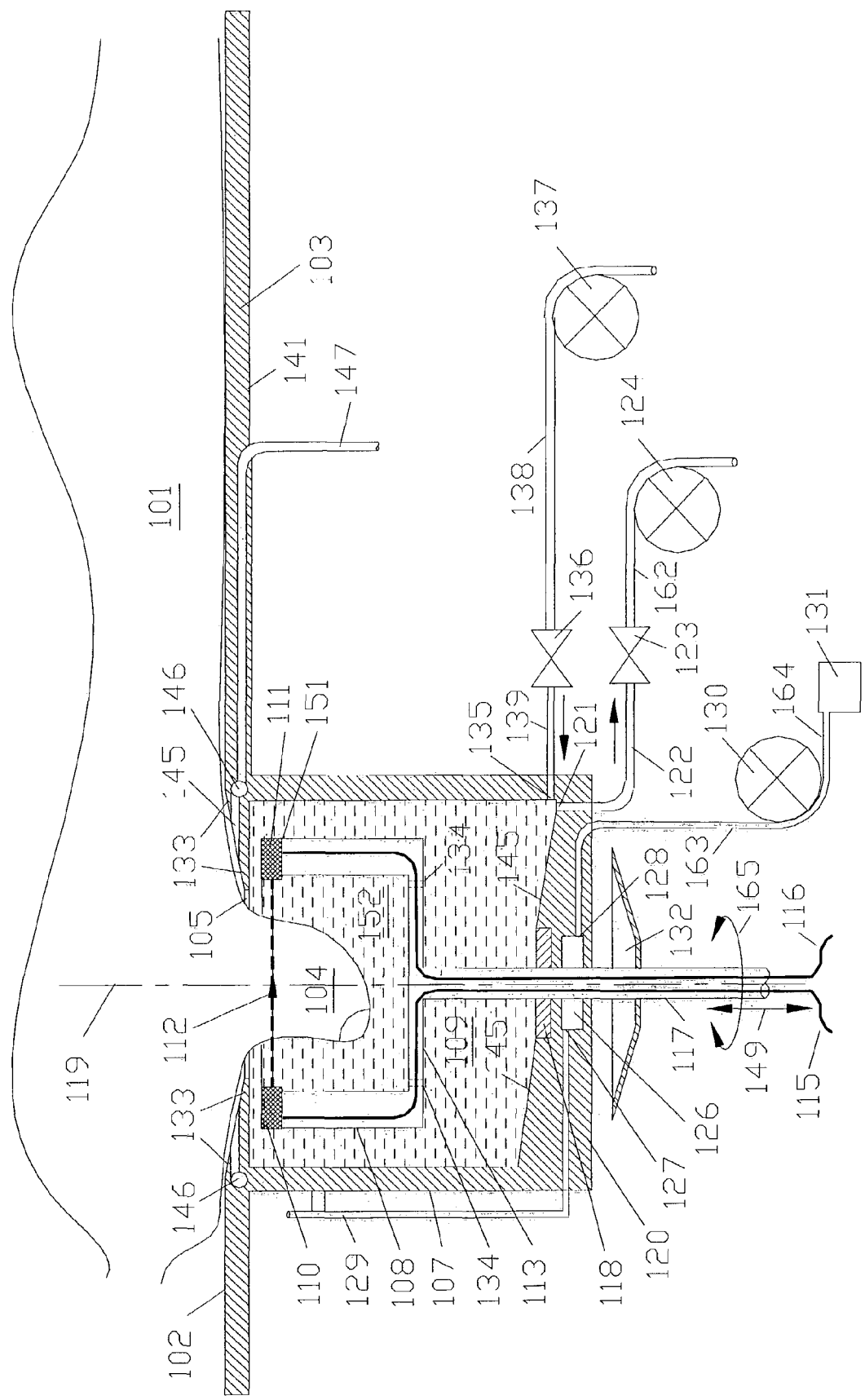
FIG. 1 illustrates various components that may be used in a breast tomography scanner.

FIG. 1 illustrates various components that may be used in a breast tomography scanner.

As shown in FIG. 1, a female subject 101 may lie in the prone position on a top surface 102 of a table 103. A breast 104 of the female subject 101 may be dangled through an opening 105 in the table 103.

The opening 105 may be circular in shape or may have a different shape. The opening 105 may include an incline 133 that tapers from the top surface 102 to at or near a bottom surface 141 of the table 103. Although shown as a straight taper, it is to be understood that other contours could be used instead for the incline 133.

The incline 133 may increase the comfort of the female subject 101, increase the hanging depth of portions of the breast 104 that are closest to the chest, thereby allowing more of these portions to be scanned, and also reduce the tendency for fluid to overflow to the top surface 102 of table 103.

The incline 133 may not extend below the level of the bottom surface 141 of the table 103. This may increase the height to which the ultrasonic transducers (discussed below) can rise, thus again maximizing the ability of the system to scan portions of the breast 104 that are closest to the chest. Other configurations and locations of the incline 133 could be used instead.

Although the opening 105 is illustrated as being tapered with an incline 133 in FIG. 1, it is to be understood that the edge could be squared or otherwise configured.

Beneath the table 103 and surrounding the opening 105 may be a stationary chamber 107 filled with a fluid 109. The stationary chamber 107 may be cylindrical, may be of another shape that has axial symmetry, or may be of another shape. It may also be integral, affixed to, detachable from, or detached from the table 103.

Within the stationary chamber 107 may be a movable chamber 108 that can be moved with respect to the stationary chamber 107. The movable chamber 108 may be cylindrical, may be of another shape that has axial symmetry, or may be of another shape. The movable chamber 108 may have its upper opening positioned beneath the opening 105 of the table 103. The movable chamber 108 may be filled with a fluid 152.

The movable chamber 108 may include an upper rim 151 at or about which are positioned one or more ultrasonic transducers, such as an ultrasonic transmitter 110 and an ultrasonic receiver 111.

The ultrasonic transducer or transducers may operate in the transmission or reflection mode. It may be a single transducer or there may be multiple transducers, such as a linear array of piezoelectric elements or a two-dimensional array of piezoelectric elements.

The ultrasonic transducers may be integral with the movable chamber 108. They may instead be contained within a separate housing that is attached at the upper rim 151 of the movable chamber 108.

FIGS. 2A-D illustrate a housing 201 that may be used in a breast tomography scanner. FIG. 2A is a perspective view of the housing 201, FIG. 2B is a side view, FIG. 2C is a top view, and FIG. 2D shows the housing 201 affixed to the top rim 151 of the movable chamber 108. A waterproof gasket or sealant may be placed between the housing 201 and the top rim 151.

As shown in FIGS. 2A-D, the ultrasonic transmitter 110 and the ultrasonic receiver 111 may be mounted within the housing 201. The housing 201 may be doughnut-shaped and have an exterior profile that substantially aligns with the exterior profile of the movable chamber 108. It may have an interior opening 250 that substantially coincides with the size of the opening for the breast in the movable chamber 108, or at least the diameter of the largest breast intended to be scanned.

The transmitter 110 and receiver 111 may be positioned such that the two are directly facing one another and such that the acoustic energy generated by the ultrasonic transmitter 110 is directed to the ultrasonic receiver 111 across the opening 250, thereby causing the breast that is inserted within this opening to be scanned during operation.

The ultrasonic transmitter 110 and the ultrasonic receiver 111 may be sized and positioned such that their apertures 210 and 211 do not protrude into the area of the opening 250. The housing 201 may include covering portions 260 on the top and bottom portions of the housing 201 to create in conjunction with the ultrasonic transmitter 110, the ultrasonic receiver 111, and semi-cylindrical adjoining walls 261 and 263 a recessed cavity. This cavity may be configured to create stagnant liquid layers in the recessed pockets, reducing turbulence in the fluid as the movable chamber 108 is rotated as described in more detail below.

FIGS. 3A-D illustrate another embodiment of a housing 301 for transducers that may be used in a breast tomography scanner. This configuration is similar to the one shown in FIGS. 2A-D, except that there are no protective covering portions on the top and bottom portions of the housing 301 and thus no associated recessed cavity. Instead, the apertures 210 of the ultrasonic transmitter 110 and 211 of the ultrasonic receiver 111 may protrude into the opening 350. This embodiment allows the opening 350 to be wider at most of its points.

Referring again to FIG. 1, a shaft 117 may be coupled to the movable chamber 108, such as at the center of the bottom 113 of the movable chamber 108. The shaft 117 may include a hollow portion in which electrical wires 115 and 116 may reside. Electrical wires 115 and 116 may be connected to the ultrasonic transmitter 110 and the ultrasonic receiver 111, respectively, through conduits in the movable chamber 108. Maintaining the wires within the conduits of the movable chamber 108 and shaft 117 may insure that they do not come in contact with the fluid 109 or 152.

Through the application of appropriate forces to the shaft 117 (discussed in more detail below in connection with FIG. 6), the movable chamber 108 may be caused to rotate about an axis 119, as indicated by rotating arrows 165. The movable chamber 108 may also be caused to move vertically, parallel to the axis 119, as reflected by movement arrows 149.

Figure 5:
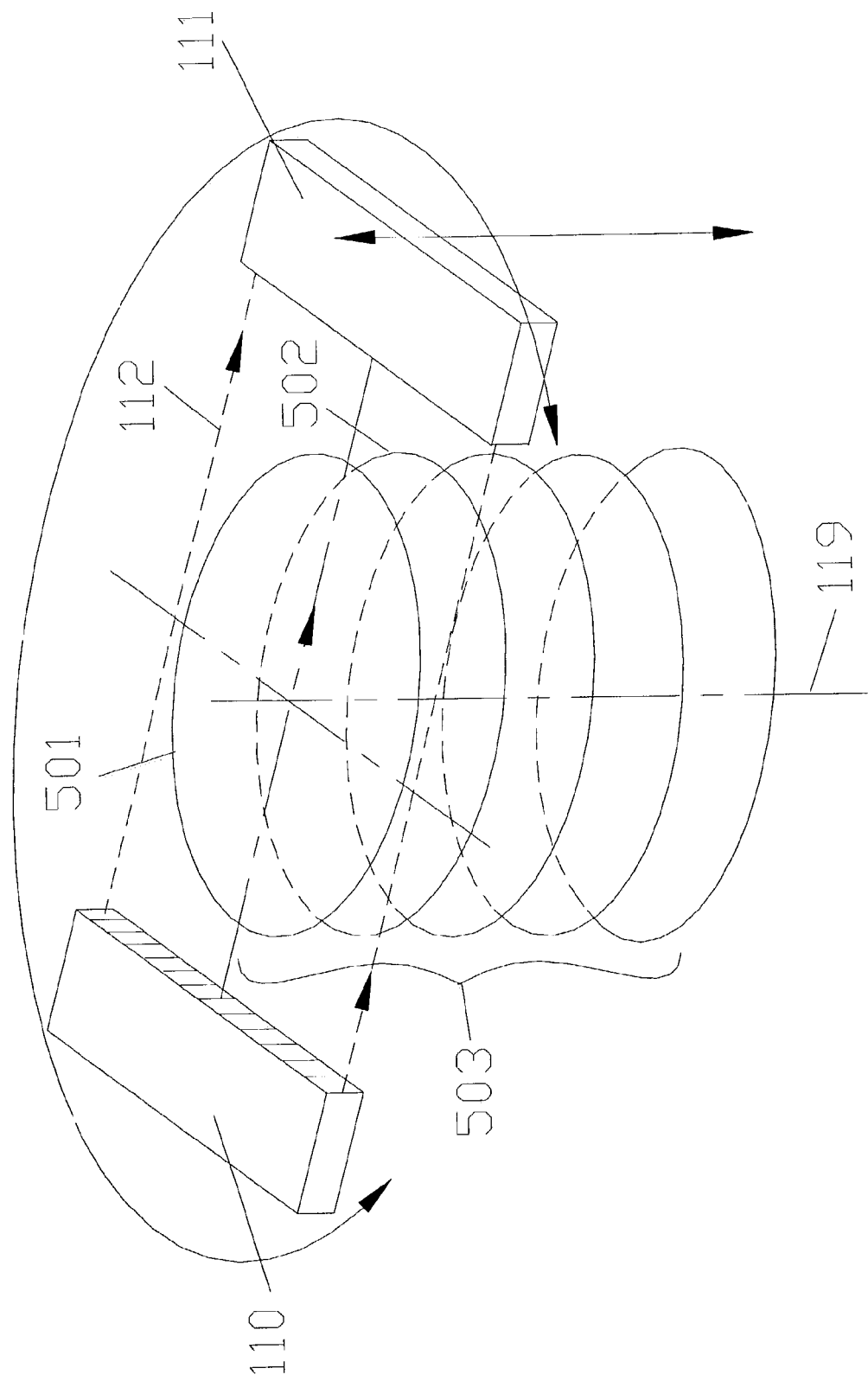
FIG. 5 illustrates a scanning pattern containing of a stacked set of tomographic images.

FIG. 5 illustrates a scanning pattern containing of a stacked set of tomographic images 503. In one mode of operation, the shaft 117 is raised until the ultrasonic transmitter 110 and the ultrasonic receiver 111 are raised as close to the chest of the female subject 101 as possible, without contacting the bottom surface 141 of the table 103. The shaft may then be operated to cause the movable chamber 108 to rotate at this vertical position. During this rotation, the ultrasonic transmitter 110 may direct ultrasonic beams 112 through the dangled breast to the ultrasonic receiver 111. The beams 112 are received during the rotation after being attenuated by the tissue in the breast by the ultrasonic receiver 111. The received projection may then be processed to create) a first two-dimensional tomographic image 501 in accordance with well-known processing techniques.

Following the acquisition of the first two-dimensional tomographic image 501, the shaft 117 may be incrementally lowered, causing the movable chamber 108 to be lowered. The shaft 117 may then be again rotated at this second vertical position, again causing the movable chamber 108 to be rotated. A second, two-dimensional tomographic image 502 may then be acquired. This process may then be repeated until the ultrasonic transducers 110 and 111 are lowered past the lowermost portion of the breast 104 that is of interest. The series 503 of tomographic images that are created may then be processed in accordance with well-known processing techniques to construct a three-dimensional image of the breast 104.

Other movement sequences may also or instead be used. For example, the shaft 107 may be rotated and moved vertically at the same time causing the ultrasonic transducers to sweep a helical path.

Fluid may be pumped into the stationary chamber 107 and, in turn, into the movable chamber 108, by a filling pump 137 communicating through a tube 138 with a controllable valve 136 and through another tube 139 to a fluid inlet 135 at the base of the stationary chamber 107.

The amount of fluid that is pumped into the stationary chamber 107 and the movable chamber 108 may vary. In one embodiment, the movable chamber 108 may be configured to hold fluid up to a first level, while the stationary chamber 107 may be configured to hold fluid up to a level that is higher than the first level. In this embodiment, fluid pumped into the stationary chamber 107 may rise above the level of the movable chamber 108 and flow over the upper rim 151 into the movable chamber 108. This may reduce turbulence that might otherwise be caused as the movable chamber 108 is lowered vertically by the shaft 117 during the scanning process.

Fluid-communication channels 134, such as holes, may also be placed in the bottom 113 of the movable chamber 108 to allow fluid to flow between the movable chamber 108 and the stationary chamber 107. These channels may also be placed in the side-walls of the movable chamber 108.

Communication channels 134 may help to reduce turbulence in the fluid during the scanning process. The communication channels 134 may be positioned as close to the outer corners of the bottom 113 of the movable chamber 108, such as next to the outer wall when placed in the bottom 113 or next to the bottom 113 when placed in the outer wall. Communication channels 134 may also make it easier to drain the movable chamber 108 (as described in more detail below) and may minimize air bubbles that otherwise might occur during filling.

A drain 121 may also be provided at the bottom 120 of the stationary chamber 107 to drain the fluids 109 and 152. The drain 121 may be connected by a tube 122 to a controllable valve 123 which, in turn, may be connected by a tube 162 to a suction pump 124. Although the drained fluid could be reused, it could instead be disposed of for sanitary reasons. To maximize the amount of fluid that is drained, the bottom surface 145 of the stationary chamber 107 may be slanted to direct the fluid toward the drain 121.

Efforts may be made to minimize leakage of fluid between the shaft 117 and the stationary chamber 107. One such effort is to include a leak-resistant bearing 118 between the two.

Fluid may still leak between the shaft 117 and the stationary chamber 107. In anticipation of this possibility, a fluid collection chamber 126 may be provided beneath the leak-resistant bearing 118, either integral to the stationary chamber 107 as shown, or separated from it. To remove any fluid that collects in the fluid-collection chamber 126, a fluid outlet 128 may be provided that is connected by a tube 163 to a suction pump 130 which, in turn, may be connected by a tube 164 to reservoir 131.

If desired, appropriate fluid sensors can be included in the fluid collection chamber 126 to cause the suction pump 130 to be activated only when fluid is detected in the fluid-collection chamber 126. The pump 130 may instead run continuously to insure that any fluid that may leak into the fluid-collection chamber is removed immediately.

Appropriate sensors may also be provided in the reservoir 131 to signal when there is leakage and/or when the reservoir must be emptied. Tube 164 may instead be connected to a drain.

To avoid a vacuum forming in the fluid-collection chamber 126 while collected fluid is being expelled by the suction pump 130, an air inlet tube 129 may be connected to an air inlet 127 at one end and exposed at the other end to air.

As an additional or different type of leak protection system, a leak collection and detection tray 132 may also be provided.

FIGS. 4A and 4B illustrate a leak collection and detection tray 132 that may be used in a breast tomography scanner. As shown in FIGS. 4A and 4B, the leak collection and detection tray 132 may include an opening 401 through which the shaft 117 passes. It may also include a water sensor, such as an interlaced mesh of bare wires 404 and 405. These wires may be insulated from the tray 132. When the tray is wet by leaking fluid, the resistance between the intermesh of bare wires 404 and 405 may drop, and this drop in resistance may be detected over a pair of detection wires 406.

Referring again to FIG. 1, protection may be provided to insure that fluid does not flow onto the top 102 of the table 103. Such protection may include one or more overflow drain holes 145 between the top surface 102 and the bottom surface 141 of the table 103. The drain holes 145, in turn, may communicate with a circumferential collection channel 146 that drains into an overflow draining tube 147.

The fluid 109 and 152 may be an acoustical coupling fluid and may include a biologically safe surfactant material to reduce its surface tension with the breast 104 and the movable chamber 108.

The surfaces within the movable chamber 108, as well as the surface of the shaft 117, may be smooth and coated with a hydrophobic paint to reduce the fluid agitation that may be created when these surfaces are moved. The movable chamber 108 may also be made of hydrophobic plastic.

Figure 6:
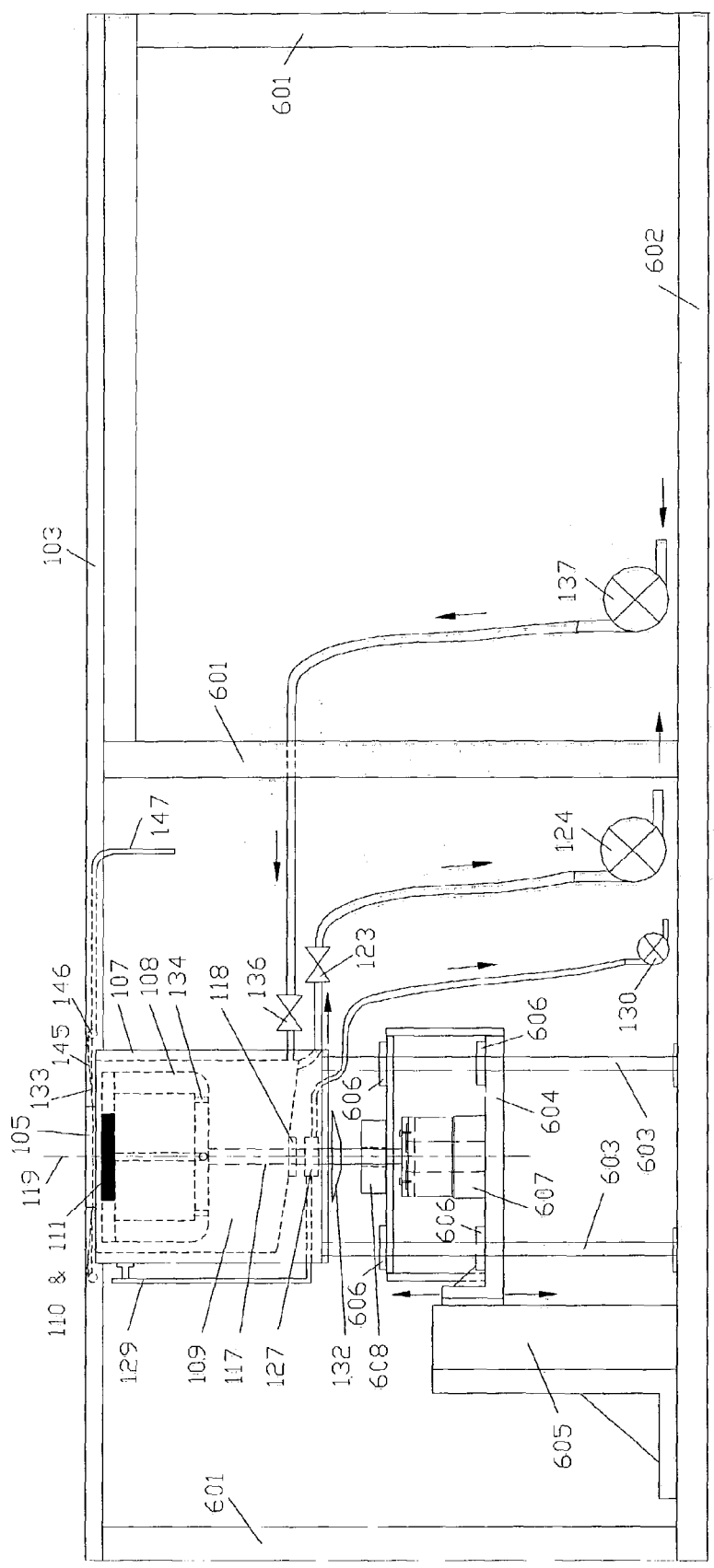
FIG. 6 illustrates additional components that may be used in a breast tomography scanner.

FIG. 6 illustrates additional components that may be used in a breast tomography scanner.

As shown in FIG. 6, the scanner may include one or more vertical columns 801 that support the table 103 and the internal components of the scanner.

The scanner may also include guide rails 603 that support the stationary chamber 107 and act as guides for the vertical translation of a stage 604.

A controlled, linear translation motor assembly 605 may be connected to the stage 604 to raise and lower the stage, so as to control its vertical position. Bearings 606 may be included for smooth sliding of the stage 604 on the guide rails 603.

The stage 604 may carry a computer-controlled motor assembly 607 that is coupled to the shaft 117. The stage 604 may also include a slip-ring assembly 608. The rotating portion of the slip-ring assembly 608 may be connected to the electrical wires 115 and 116 shown in FIG. 1, while the stationary portion of the slip-ring assembly 608 may be connected to corresponding stationary electrical wires for delivering and picking up signals from the wires 115 and 116, respectively.

In lieu of the slip-ring assembly 608 or a similar connection system, the motor assembly 607 may be driven so as to merely cause the movable chamber 108 to rotate back and forth, like the agitator in a washing machine. In this embodiment, the slip-ring assembly 608 may be replaced by a loose coil of the cables 115 and 116. This latter approach might reduce the complexity of the electrical connections and the susceptibility of the system to electrical noise.

Figure 7:
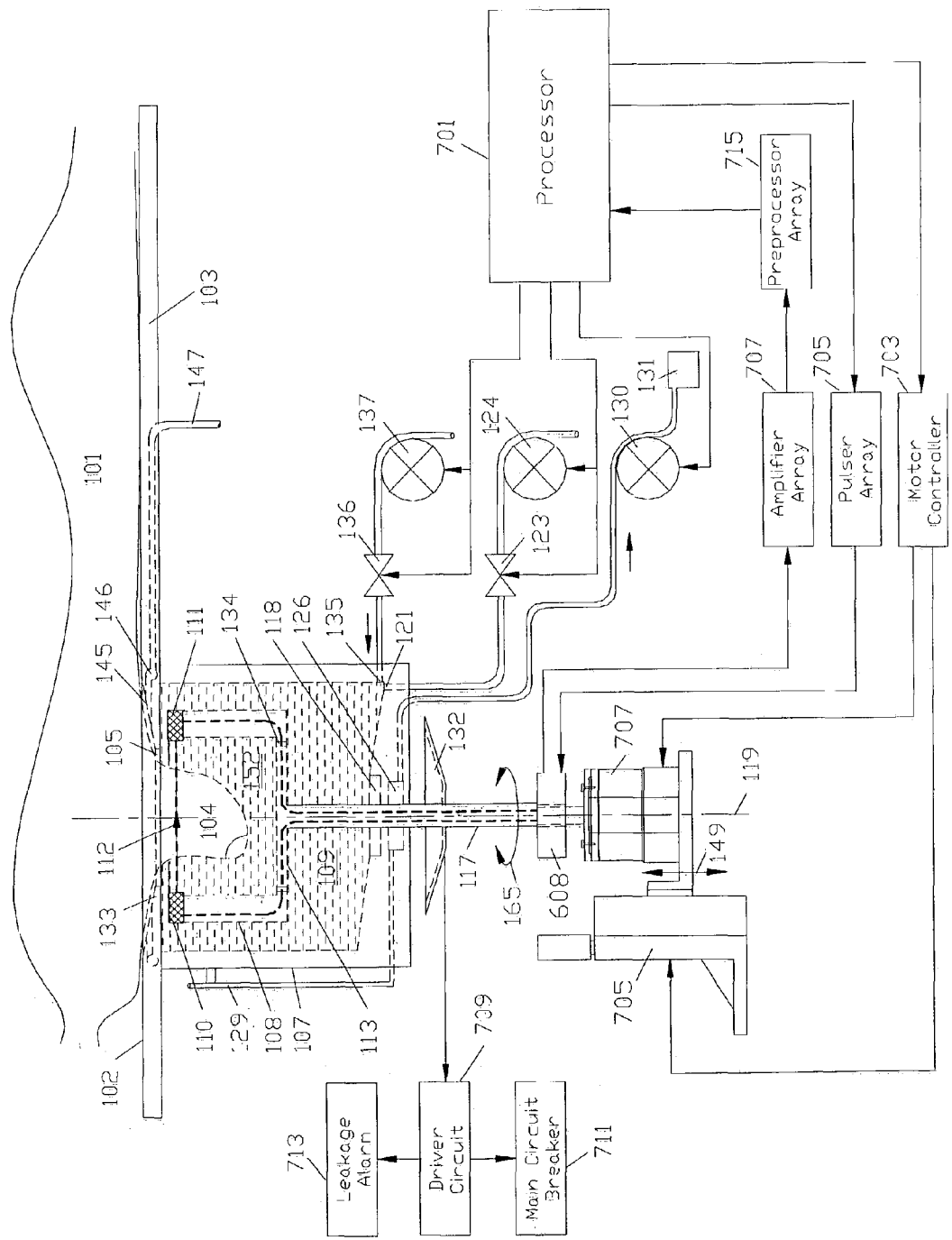
FIG. 7 illustrates electronics that may be used in a breast tomography scanner.

FIG. 7 illustrates electronics that may be used in a breast tomography scanner. A processor 701 may start the imaging session by causing the filling valve 136 to open and the filling pump 137 to begin pumping fluid into the stationary chamber 107. A pre-determined volume of fluid may be pumped or liquid level sensors (not shown) may be placed near the rim of the breast opening 105 to detect when the chambers are full.

After the fluid filling process begins, the processor 701 may energize the suction pump 130 to insure that fluid does not leak into the lower portions of the scanner and in the vicinity of the electronics. The processor 701 may cause the suction pump to run throughout the filling and scanning process and until the fluid is later emptied. The processor 701 may instead be connected to a sensor positioned within the fluid collection chamber 126 and only energize the suction pump 130 when the fluid sensor detects the presence of fluid within the fluid collection chamber 126.

Once the stationary chamber 107 and movable chamber 108 have been fully filled with fluid, the processor 701 may deliver ,instructions to a motor controller 703 to cause the linear translation motor assembly 705 and the computer-controlled rotor motor assembly 707 to raise the movable chamber 108 to its highest position.

The processor 701 may then cause a pulser array 705 to generate excitation pulses that are delivered through the slip-ring assembly 608 to the ultrasonic transmitter 110. The ultrasonic signals generated by the ultrasonic transmitter 110 may then pass through the breast 104 to the ultrasonic receiver 111. The received signals may be converted to electrical signals by the ultrasonic receiver 111 and delivered through the slip-ring assembly 608 to an amplifier array 707 and then a pre-processor array 715 to create a projection.

The processor 701 may then signal the motor controller 703 to cause the movable chamber 108 to incrementally rotate, following which a second projection is created. This processor may repeat this process until the moving chamber 108 has gone through an entire rotation, following which the set of projections obtained during this rotation may be combined using know techniques to create a tomographic image of a slice of the breast 104.

The processor 701 may then direct the motor controller to incrementally lower the movable chamber 108, followed by instructions that would create a tomographic image of a second slice of the breast 104. This process may repeat until all portions of interest in the breast have been scanned. The tomographic images may then be combined using well known techniques to create a three-dimensional image of the breast.

The processor 701 may instead issue instructions to the motor controller 703 to cause the ultrasonic transducers to traverse a helix. Other scan patterns may also be used.

The ultrasonic receiver 111 may have embedded, or included in close proximity, one or more pre-amplifiers to boost the electrical signals prior to their transmission to the slip-ring assembly 708.

Although not shown, it is to be understood that the processor 701 may be in communication with the motor controller 703, the motor 705, the motor 707, and/or with movement sensors in the vicinity of the movable chamber 108 so as to provide a means to synchronize the signals that are received by the ultrasonic receiver 111 with the rotational and translational movement of the ultrasonic transducers. The processor 701 may cause the movable chamber 108 to move in increments movements and to cause a measurement of the signal received by the acoustic receiver 111 after each incremental movement, as discussed above, or it may instead and/or in addition cause the movable chamber 108 to continuously rotate and/or vertically translate.

The end of the scanning process may be signaled by the detection of a dramatic change in the nature of the signal received by the acoustic receiver 111, by a position-sensing switch near the bottom of the stationary chamber 107, or in an open-loop manner by completion of a pre-programmed set of commands that the processor 701 sends to the motor controller 703.

Whatever the method, the processor 701 at the end of the scan may direct the draining valve 123 to open and the draining pump 124 to energize. The completion of the draining process could be dictated in an open-loop manner by a timer or in a closed-loop manner by a sensor that senses the absence of fluid in the stationary chamber 107.

The sensor on the leak collection and detection tray 132 may be in communication with a driver circuit 709 that detects the presence of fluid on the leak collection and detection tray 132 throughout filling, imaging and draining process. If fluid is detected at any point, a main circuit breaker 711 may be opened, shutting down power to the system, and a battery-operated leakage alarm 713 may be sounded.

Although certain features, benefits and embodiments have now been described, it is to be understood that this application is not limited to these features, benefits and embodiments, but solely to the subject matter delineated by the following claims and its equivalents.

I claim:

1. A breast tomography scanner comprising:
a stationary chamber configured to hold fluid;
a movable chamber within the stationary chamber configured to hold fluid, to rotate about a vertical axis within the stationary chamber, to have at least one opening other than its top and to receive a breast, wherein the opening is patent at all times to allow fluid communication between the movable and the stationary chamber; and
an ultrasonic breast scanning apparatus having a transmitter and a receiver coupled to the movable chamber, configured to scan the breast received by the movable chamber.

2. The breast tomography scanner of claim 1, wherein the movable chamber has an upper rim and wherein the ultrasonic transmitter and the ultrasonic receiver are located at the upper rim.

3. The breast tomography scanner of claim 2, further including a donut-shaped housing configured to be affixed to the top of the rim of the movable chamber in which the ultrasonic transmitter and ultrasonic receiver are contained.

4. The breast tomography scanner of claim 3, wherein the housing includes a recessed cavity surrounding the ultrasonic transmitter and ultrasonic receiver.

5. The breast tomography scanner of claim 1, wherein the movable chamber is configured to move longitudinally along the vertical axis.

6. The breast tomography scanner of claim 1, wherein the movable chamber has a plurality of openings other than at its top configured to allow fluid to flow between the movable chamber and the stationary chamber.

7. The breast tomography scanner of claim 6, wherein the movable chamber has a bottom and wherein the plurality of openings are located in the bottom.

8. The breast tomography scanner of claim 7, wherein the movable chamber has a cylindrical wall and wherein the plurality of openings are located adjacent the wall.

9. The breast tomography scanner of claim 6, wherein the movable chamber has a cylindrical wall and wherein the plurality of openings are located in the cylindrical wall.

10. The breast tomography scanner of claim 9, wherein the movable chamber has a bottom and wherein the plurality of openings are located adjacent the bottom.

11. The breast tomography scanner of claim 1, further including a shaft extending through the stationary chamber configured to be affixed to the movable chamber.

12. The breast tomography scanner of claim 11, further including a leak-resistant bearing between the shaft and the stationary chamber.

13. The breast tomography scanner of claim 12, further including a collection chamber configured to be positioned beneath the leak-resistant bearing and configured to collect fluid that leaks past the leak-resistant bearing.

14. The breast tomography scanner of claim 13, further including a suction device connected to the collection chamber to remove fluid collected in the collection chamber.

15. The breast tomography scanner of claim 13, further including a leak collection tray configured to be positioned beneath the collection chamber to collect fluid that leaks past the collection chamber.

16. The breast tomography scanner of claim 15, further including an alarm in communication with the collection tray and configured to sound in the event that fluid leaks onto the leak collection tray.

17. The breast tomography scanner of claim 15, further including a power shut off circuit in communication with the collection tray and configured to remove power from the breast tomography scanner in the event that fluid leaks onto the leak collection tray.

18. The breast tomography scanner of claim 11, wherein the shaft has an interior and wherein the breast scanning apparatus includes electrical wires attached to the ultrasonic transducer that pass though the interior of the shaft.

19. The breast tomography scanner of claim 18, wherein the electrical wires are attached to a slip ring assembly mounted to the shaft.

20. The breast tomography scanner of claim 1, wherein:
the movable chamber is configured to hold a fluid up to a first level;
the stationary chamber is configured to hold fluid up to a second level; and
wherein the second level is higher than the first level.

21. The breast tomography scanner of claim 20, further including:
a chamber filling pump configured to cause fluid to fill the movable chamber and the stationary chamber; and
a processor configured to control the operation of the chamber filling pump such that the chamber filling pump causes the fluid level in both the movable chamber and the stationary chamber to exceed the first level but not the second level.

22. The breast tomography scanner of claim 21, wherein the stationary chamber and the movable chamber are configured such that the level of fluid within both of them equalizes.

23. The breast tomography scanner of claim 1, further including: a table top having a top surface and a bottom surface positioned above the movable chamber; and an opening in the table top extending from the top surface to the bottom surface, positioned above the movable chamber, and configured to receive a breast.

24. The breast tomography scanner of claim 23, further including a drain positioned under the top surface of the table and configured to prevent fluid from flowing from the stationary chamber or movable chamber to the top surface of the table.

25. The breast tomography scanner of claim 24, wherein the drain is positioned between the top and bottom surface of the table top and is in fluid communication with the opening.

26. The breast tomography scanner of claim 23, wherein the top surface but not the bottom surface is tapered downwardly in the area of the opening.

27. The breast tomography scanner of claim 1, further including acoustic coupling fluid in the stationary chamber and the movable chamber that includes a surfactant.

28. The breast tomography scanner of claim 1, further including: a drain at the bottom of the stationary chamber to drain fluid from the chamber; and a slanted surface at the bottom of the stationary chamber configured to direct fluid towards the drain.

* * * * *